March 3, 1964 H. BRANDT Plant Pat. 2,368
HEMLOCK TREE
Filed April 2, 1962
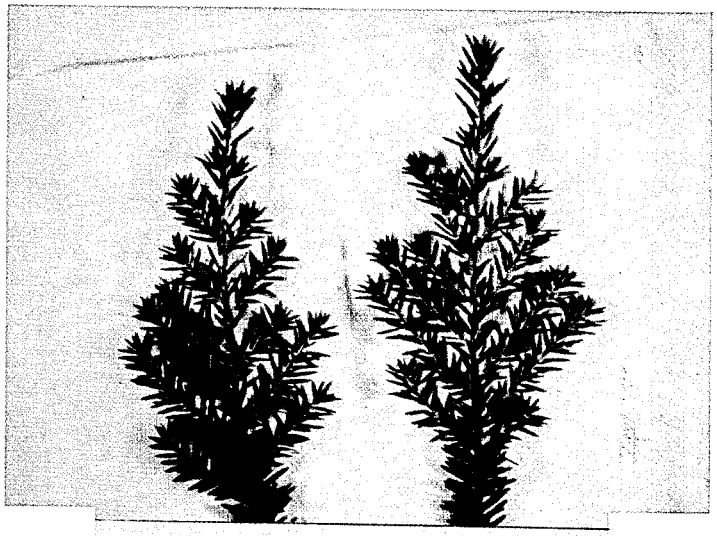
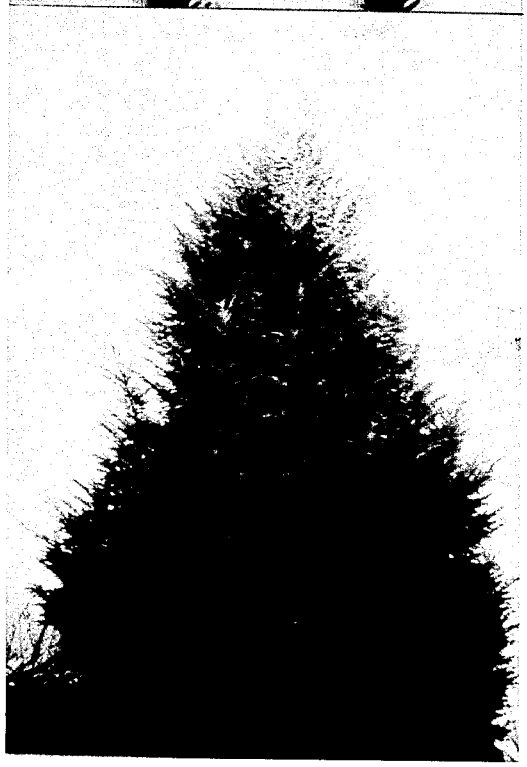
INVENTOR
Herman Brandt
BY Robb & Robb
ATTORNEYS United States Patent Office Plant Pat. 2,368
Patented Mar. 3, 1964

2,368
HEMLOCK TREE

Herman Brandt, Valley Cottage, N.Y.

Filed Apr. 2, 1962, Ser. No. 184,617
1 Claim. (Cl. Plt.—50)

The present invention relates to a new and distinct variety of hemlock tree which originated as a selected cultivated seedling derived from seeds of an unidentified and unpatented hemlock tree of the species botanically known as *Tsuga canadensis,* said seeds having been planted and grown by me on cultivated property under my control and supervision at Valley Cottage, Rockland County, New York. The original seeds resulted from open pollination of the parent hemlock tree, and the seedlings derived therefrom were carefully selected and ultimately confined to the single seedling which I selected because of its new, improved and unique combination of characteristics never previously exhibited in any hemlock tree of which I am aware.

The novelty and distinctiveness of my new hemlock tree are evidenced by the following outstanding characteristics which differentiate it from the common species *Tsuga canadensis,* as well as from all other varieties:

(1) An extremely rapid and vigorous habit of growth, averaging tip growth of about 34 inches per year and attaining a height of over 100 inches in ten years, as compared with an average yearly growth of about 8 inches and a height of from about 52 inches to 72 inches in ten years in the case of the normal variety known as *T. canadensis;*

(2) Good hardiness;

(3) A habit of continuous growth from May to September under normal conditions, as distinguished from the usual intermittent growing seasons, commonly referred to as "flashes" of growth, which occur in late spring and late summer, respectively, with little or no growth in between, in the case of ordinary hemlock trees including those of *T canadensis.*

(4) A habit of developing numerous branchlets on the sides of current growth, with a resultant heavier, denser and very compact type of growth resembling a clipped hemlock, without actual pruning;

(5) Exceptionally abundant foliage averaging from approximately 2 to 3 times as many leaves per unit of stem as compared with the regular species *Tsuga canadensis;*

(6) A distinctive deeper green color of the leaves which persists throughout the year, as compared with *T. Canadensis, T. canadensis compacta*—variations #1, 2#, #3 and #7, *T. canadensis* coplen's pyramidal and *T. Candensis dawsoniana,* all of which have a lighter green winter color; shows less yellowing or browning of the foliage than common hemlock under similar conditions of winter exposure; and (7) Greater success in rooting of cuttings than with any common hemlocks of which I am aware, including those mentioned above.

Asexual reproduction of my new hemlock variety by cuttings, as performed by me at Valley Cottage, New York, shows that the foregoing characteristics and distinctions come true and are established and transmitted through succeeding propagations.

The accompanying drawing shows a typical specimen tree of my new hemlock variety, as well as portions of the foliage on a somewhat enlarged scale, with the latter foliage specimens respectively showing the upper and under surfaces of the foliage, all as depicted in color as nearly true as it is reasonably possible to make the same in a color illustration of this character.

The following is a detailed description of my new hemlock variety, with color terminology in accordance with Ridgway's Color Standards and Nomenclature, except where general color terms of ordinary dictionary significance are obvious, as based upon observations made from specimen trees grown at Valley Cottage, New York.

Parentage: An open-pollinated seedling of the species *Tsuga canadensis.*

Type: Hardy; upright; outdoor; seedling; ornamental evergreen; for use in ornamental garden plantings.

Propagation: Holds its distinguishing characteristics through succeeding propagations by cuttings.

Habit of growth: Broad; compact; pyramidal.

Trunk: Upright; naturally maintains a main leader; color of bark same as regular *Tsuga canadensis.*

Branches: Sturdy; more than average number than in regular hemlocks; with yellow-brown pubescence.

Foliage: Evergreen; flat; grooved above and with 2 pale bands below; from 8 to 18 mm. long.

*Color.*—Young: upper side—Dark Cress Green, Plate XXXI, 29, *m.*; under side—Dull Yellow Green (1), Plate XXXII, 31, *k.* Mature: upper side—Varley's Green, Plate XVIII, 31, *m.*; under side—Varley's Green, Plate XVIII, 31, *m.*

Flower: Has not flowered.

Fruit: Has not fruited.

Disease resistance: Highly resistant to all diseases to which hemlock trees and plants are generally subject, as determined by comparison with other varieties grown under comparable cultural conditions at Valley Cottage, Rockland County, New York.

I claim:

A new and distinct variety of hemlock tree, substantially as herein shown and described, characterized particularly as to novelty by an extremely rapid and vigorous habit of growth, extremely good hardiness, an unusual habit of continuous growth from May to September under normal conditions, a habit of developing numerous branchlets on the sides of current growth, with attendant heavier, denser and very compact growth resembling a clipped hemlock without actual pruning, exceptionally abundant foliage, and a distinctive deep green color of the foliage which persists throughout the entire year with little yellowing or browning by winter exposure, with a consequent truly evergreen habit and a darker than normal color of the foliage as compared with regular hemlocks.

No references cited.